United States Patent
Lever et al.

(10) Patent No.: US 6,455,610 B1
(45) Date of Patent: Sep. 24, 2002

(54) ANTIMICROBIAL PRE-VULCANIZED RUBBER COMPOSITIONS

(75) Inventors: John G. Lever, Spartanburg, SC (US); Geoffrey R. Haas, Spartanburg, SC (US); Bhawan Patel, Bolton (GB)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 09/815,730

(22) Filed: Mar. 23, 2001

(51) Int. Cl.$^7$ .............................. C08K 5/09; C08K 3/10; C08K 3/34

(52) U.S. Cl. ..................... 523/122; 524/287; 524/403; 524/492

(58) Field of Search ........................... 523/122; 524/287, 524/403, 492

(56) References Cited

U.S. PATENT DOCUMENTS

| | | | | |
|---|---|---|---|---|
| 5,441,717 A | | 8/1995 | Ohsumi et al. | 423/306 |
| 5,466,726 A | | 11/1995 | Inoue et al. | 523/122 |
| 5,698,229 A | * | 12/1997 | Ohsumi et al. | 424/604 |
| 5,968,229 A | | 12/1997 | Ohsumi et al. | 424/604 |
| 5,736,591 A | | 4/1998 | Dunn | 523/122 |

FOREIGN PATENT DOCUMENTS

| | | |
|---|---|---|
| JP | 7-194661 | 8/1995 |
| JP | 8-205985 | 8/1996 |
| JP | 8-239577 | 9/1996 |
| JP | 10-329864 | 12/1996 |
| JP | 10-217261 | 8/1998 |
| JP | 11-158328 | 6/1999 |

OTHER PUBLICATIONS

AATCC Test Method Draft "Assessment of Antibacterial Properties on Hydrophobic Textiles and Solid Substrates" (1999).
Japanese Industrial Standard JIS Z 2801:2000, "Antimicrobial products—Tests for antimicrobial activity and efficacy".

* cited by examiner

Primary Examiner—Kriellion A. Sanders
(74) Attorney, Agent, or Firm—Terry T. Moyer; William S. Parks

(57) ABSTRACT

Certain non-silicone pre-vulcanized raw rubber formulations that include silver-based compounds to provide highly desirable long-term antimicrobial characteristics within the ultimate cured rubber articles made therefrom are provided. Such formulations are intended to be vulcanized to provide solid or blown (foam or sponge) rubber articles which can be utilized in a variety of different applications (as well as multi-layered composites including such antimicrobial rubber. As silver-based compounds are deleteriously affected by utilization of standard curing agents and curing accelerators, such as sulfur-based compounds and/or systems, the ability to provide such an effective antimicrobial vulcanized rubber article is rather difficult. However, this invention encompasses the presence of different non-sulfur-based curing systems and curing agents, such as inorganic and organic peroxides and oxides, as some examples, that permit vulcanization and do not irreversibly bind silver ions thereto, thereby resulting in long-term antimicrobial performance of the ultimate rubber article itself. The raw rubber formulations may also comprise fillers and may also include plasticizers to provide desired characteristics of dimensional stability, stiffness, flexural modulus, tensile strength, abrasion resistance, elongation, and the like, for the ultimate rubber article, while simultaneously and surprisingly enhancing the control of antimicrobial efficacy in the rubber article as well.

27 Claims, No Drawings

ANTIMICROBIAL PRE-VULCANIZED RUBBER COMPOSITIONS

FIELD OF THE INVENTION

This invention relates to certain non-silicone pre-vulcanized raw rubber formulations that include silver-based compounds to provide highly desirable long-term antimicrobial characteristics within the ultimate cured rubber articles made therefrom. Such formulations are intended to be vulcanized to provide solid or blown (foam or sponge) rubber articles which can be utilized in a variety of different applications (as well as multi-layered composites including such antimicrobial rubber. As silver-based compounds are deleteriously affected by utilization of standard curing agents and curing accelerators, such as sulfur-based compounds and/or systems, the ability to provide such an effective antimicrobial vulcanized rubber article is rather difficult. However, this invention encompasses the presence of different non-sulfur-based curing systems and curing agents, such as inorganic and organic peroxides and oxides, as some examples, that permit vulcanization and do not irreversibly bind silver ions thereto, thereby resulting in long-term antimicrobial performance of the ultimate rubber article itself. The raw rubber formulations may also comprise fillers and may also include plasticizers to provide desired characteristics of dimensional stability, stiffness, flexural modulus, tensile strength, abrasion resistance, elongation, and the like, for the ultimate rubber article, while simultaneously and surprisingly enhancing the control of antimicrobial efficacy in the rubber article as well.

DISCUSSION OF THE PRIOR ART

All U.S. Patents listed below are herein entirely incorporated by reference.

There has been a great deal of attention in recent years given to the hazards of microbial contamination from potential everyday exposure. Noteworthy examples of such concerns include the fatal consequences of food poisoning due to certain strains of *Eschericia coli* being found within undercooked beef in fast food restaurants; *Salmonella enteritidis* contamination causing sicknesses from undercooked and unwashed poultry food products; and illnesses and skin infections attributed to *Staphylococcus aureus, Klebsiella pneumoniae*, yeast (*Candida albicans*), and other unicellular organisms. With such an increased consumer interest in this area, manufacturers have begun introducing antimicrobial agents within various everyday products and articles. For instance, certain brands of cutting boards, , shoe inserts, medical devices and implements, liquid soaps, etc., often contain antimicrobial compounds. The most popular antimicrobial agent for such articles is triclosan. Although the incorporation of such a compound within a liquid or certain polymeric media has been achieved, other substrates, specifically vulcanized rubber and surfaces thereof, have proven less accessible. For instance, triclosan itself diffuses easily within and out of polymeric substrates and/or matrices,and thus is not very durable. Furthermore, triclosan lacks the desired thermal stability for plastic processing at high temperatures, and does not provide a wide range of bacterial kill. For instance, triclosan does not exhibit any kill for *Pseudomonas aeruginosa*.

Antimicrobial raw rubber formulations are certainly highly desired for the production of vulcanized rubber articles to provide not only antibacterial benefits, but also antifungal, antimildew, antistaining, and odor control properties. Rubber articles are utilized in many different applications, including automobiles (hoses, tires, bumpers, etc.), food processing equipment (conveyor belts, wheels, tubing, gaskets), household items (toys, sink washers, gaskets, appliances, rubber door mats, rubber floor mats, carpeted floor or door mats, gloves, and the like), basically any rubber applications in which bacterial and fungal growth is a potential problem. There thus remains a long-felt need to provide an effective, durable, reliable antimicrobial vulcanized rubber formulation which will provide such long-term antimicrobial and/or antifungal effects within the final vulcanized rubber article. Unfortunately, such a highly desired antimicrobial raw rubber formulation and/or vulcanized rubber article comprising silver-based antimicrobial agents has heretofore not been provided by the pertinent prior art.

The closest art includes Japanese Patent Application 1997-342076 which discloses the production of unvulcanized rubber formulations and articles exhibiting antibacterial properties due to the presence of silver complexes. Such formulations are formed through high temperature kneading in an oxygen-free atmosphere and are used as parts in a water disinfection system. Again, no vulcanized rubber is taught or obtained within or through this disclosure. Antimicrobial rubber bands have been taught in Japanese Patent Application 1997-140034 in vulcanized form with silver antimicrobials therein. However, such compounds are rather limited in use and the vulcanization step must include a sulfur curing agent to effectuate the final vulcanized arrangement of the subject rubber. Such sulfur curing agents have a remarkably deleterious effect on certain silver-based antimicrobials such that the sulfur reacts with the silver ion, to form silver sulfide, thus rendering it ineffective as a bactericide. As such, the utilization of such specific rubber band formulations for and within large-scale antimicrobial articles is basically unworkable.

Certain types of antimicrobial peroxide-catalyst vulcanized rubber formulations have been produced in the past; however, such peroxide-cured rubbers are all silicone-based. It is well understood and accepted that silicone rubbers cannot be vulcanized by typical sulfur-based catalysts. Thus, the antimicrobial rubber formulations of Japanese Patent Applications 1997-026273 and 1995-065149 as well as U.S. Pat. No. 5,466,726 are standard vulcanized silicone rubber formulations and articles which also include certain antimicrobial compounds.

Furthermore, rubber latexes (non-vulcanized) comprising antimicrobials have been disclosed (U.S. Pat. No. 5,736,591, for example), as have floor mats having silver-based antimicrobials incorporated within pile fiber components and which have non-antimicrobial rubber backings cured through peroxide-catalyzed vulcanization to protect the pile fiber antimicrobial compounds from attack by any sulfur compounds (as in Japanese Patent Applications 1993-3555168 and 1995-38991). Again, however, to date there have been no disclosures or suggestions of producing a non-silicone raw rubber formulation or vulcanized rubber article made therefrom exhibiting excellent antimicrobial properties through the long-term effective utilization of silver-based antibacterial compounds. This invention fills such a void.

OBJECT OF THE INVENTION

It is therefore an object of this invention to provide an antimicrobial substantially non-silicone pre-vulcanized raw rubber formulation that ultimately provides a vulcanized non-silicone rubber article of sufficient antimicrobial activity and structural integrity to withstand repeated use without losing an appreciable level of either antimicrobial efficiency or modulus strength. Another object of the invention is to ultimately provide an antimicrobial non-silicone pre-vulcanized rubber formulation comprising silver-based antimicrobial compounds which include curing agents and curing accelerators which do not deleteriously effect the antimicrobial activity of the ultimate vulcanized rubber article (and thus is essentially free from sulfur-based curing agents and accelerators). Yet another object of this invention is to provide an unvulcanized non-silicone raw rubber formulation that, upon vulcanization, cures to form such an antimicrobial non-silicone vulcanized rubber article exhibiting log kill rates for *Staphylococcus aureus* and *Klebsiella pneumoniae* (and/or other types of bacteria as well) of at least 1.0 after 24 hours exposure at room temperature. Still another object of the invention is to provide an unvulcanized rubber formulation that, upon vulcanization, cures to form an antifungal article exhibiting at least 70% inhibition in accordance with Test Method ISO 486, of *Aspergillus niger*, *Paecilomyces variotii*, and *Trichoderma virens* (and/or other types of fungi as well) for at least 15 days at 30° C. and at greater than 90% humidity. Still another object of this invention is to provide an unvulcanized non-silicone raw rubber formulation comprising structural integrity filler components (e.g., carbon black, silica, metal salts, organic salts, metal oxides, and the like) and plasticizers (e.g., phthalate oil, paraffinic oil, and the like) that provide enhancements in the control of antimicrobial efficacy of such a rubber article through controlled silver ion release to the article surface. Still another object of the invention is to provide a finished article that exhibits increases in antimicrobial activity after industrial washing and/or abrasion.

Accordingly, this invention encompasses a non-silicone unvulcanized raw rubber formulation comprising at least one rubber constituent, at least one silver-based antimicrobial compound, and at least one curing catalyst compound, wherein said catalyst does not include an appreciable amount of sulfur-based curing agent and/or accelerator compound or compounds, and wherein said rubber formulation optionally comprises a blowing agent, and at least one filler component. Such a raw rubber formulation can be subsequently cured (vulcanized) in the presence of the substantially non-sulfur based curing agents to produce a resilient antimicrobially effective rubber article that exhibits dimensional stability.

Such a specific non-silicone raw rubber formulation has not been taught nor fairly suggested within the rubber industry or prior art. As noted above, the avoidance of sulfur-based curing agents and accelerators to any appreciable degree thus permits the retention of silver antimicrobials within the final product in amounts sufficient to provide long-lasting log kill rates for *Staphylococcus aureus, Klebsiella pneumoniae, Pseudomonas aeruginosa*, and *Eschericia coli*, at the very least. Furthermore, due primarily to high costs, non-sulfur curing agents have not been prevalent within vulcanized rubber formulations and articles. As such, there has been no teaching or fair suggestion of coupling non-sulfur curing agents (and most preferably peroxide curing agents) with silver-based antimicrobial agents within pre-vulcanized rubber formulations to form effectively antimicrobial vulcanized rubber articles.

Additionally, generally and preferably, though not necessarily, certain fillers and oils (such as silica, carbon black, stearates as fillers, and phthalate and paraffinic oils) are required to provide both flexural modulus and structural integrity to vulcanized rubber articles. The rubber component alone generally does not exhibit proper dimensional stability without such additives. Surprisingly, the presence of such additives also provides the ability to control silver-ion release at the target article surface. Without intending to be bound to any specific scientific theory, it appears that such fillers as silica and such oils as paraffinic oil (as some examples), act in such a way as to draw moisture into the article which then transports silver ions from within the article to the surface. In such a situation, then, the rubber article may exhibit enhanced silver release resulting in higher log kill rates for certain bacteria due to the presence of larger amounts of available surface silver ions. Other fillers, such as pigments (for example, carbon black) and calcium carbonate (as some examples) appear to work in the opposite manner by keeping water out of the target article and thus prevent silver-ion migration to the article surface. Thus, the reduction of such silver-ion availability increases the long term durability of the antimicrobial article. In effect, then, the actual antibacterial efficacy of the entire rubber article can be controlled through the presence of certain amounts of such generally required fillers and oils (some hydrophilic antistatic agents also appear to act in the same manner as silica as well). As a result, the necessary filler and/or oil constituents required to provide dimensional resiliency and/or flexural modulus (and thus actual usefulness) of the finished article serve a dual purpose heretofore unrecognized within the rubber industry. Rubber articles can be produced with specific end-uses in mind depending upon the duration of antimicrobial activity desired through the addition of specific amounts of such additives. Again, such a targeted duration antimicrobial vulcanized article and the benefits thereof have heretofore been unknown and unrecognized within the rubber industry. These rubber components are thus hereinafter referred to as "silver ion release control additives".

The term rubber, as noted above, is intended to cover any standard rubber which must be vulcanized to provide a dimensionally stable rubber article. The specific types are listed below and have been utilized for many years and are generally well known and taught throughout the prior art. Such inventive rubber formulations should also possess a chemical plasticizer which aids in the breakdown period of the elastomer during compounding and processing (and provides flexural modulus properties to the finished article) as well as fillers required for reinforcement (e.g. calcium carbonate, carbon black, silica, and clays). Optionally, to form a blown (foam or sponge, closed-cell, for example) rubber type, a blowing agent may be added to the inventive formulation.

The rubber component or components of the inventive raw rubber formulation is therefore selected from the group consisting of nitrile rubber [such as acrylonitrile-butadiene (NBR)], styrene-butadiene rubber (SBR), chloroprene, ethylene propylene diene comonomer (EPDM), natural rubber, polyurethane rubber, butyl rubbers, neoprene, isoprene, halobutyl rubbers, fluoroelastomers, epichlorohydrin rubber, polyacrylate rubber, and chlorinated polyethylene rubber. Modified rubbers which are potentially useful, though more expensive, include hydrogenated SBR, hydrogenated NBR, and carboxylated NBR and the like. Although the presence of silicone-rubber is discouraged within the inventive formulation, there remains the possibility of adding certain low amounts of such specific unvulcanized rubber components without adversely affecting the overall antimicrobial rubber formulation itself. Thus, up to 25% by total weight of the formulation may be silicone-rubber; however, the vast majority of the rubber formulation must be non-silicone rubber. Furthermore, the non-silicone rubber portion must not possess an appreciable amount of sulfur-based curing agent or residue (in the finished article) and thus must be vulcanized through curing with primarily non-sulfur-based compounds (such as peroxides and metal oxides, for example). The rubber component is present in amount of from about 10 to about 1,000 parts of the entire composition, more preferably from about 50 to about 500 parts, and most preferably from about 100 to about 200 parts. Thus, with a total number of parts between about 300 and 2,000 parts throughout the target pre-vulcanized rubber formulation (and subsequently formed rubber article), the rubber constitutes from about 25 to about 70% of the percentage by parts of the entire formulation (and article). The remainder comprises additives such as fillers, oils, curing agents, the desired antimicrobial agents, optional blowing agents, and the like (as discussed more thoroughly below).

Furthermore, the non-silicone rubber portion must not possess an appreciable amount of sulfur-based curing agent or residue (in the finished article) and thus must be vulcanized through curing with primarily non-sulfur-based compounds (such as peroxides and metal oxides, for example). The rubber component is present in amount of from about 10 to about 1,000 parts of the entire composition, more preferably from about 50 to about 500 parts, and most preferably from about 100 to about 200 parts.

The antimicrobial agent of the inventive raw rubber formulation may be of any standard silver-based compounds. Such compounds, in contrast with organic types, such as triclosan, for example, do not exhibit low thermal stability and thus remain within the target matrix or substrate at different temperatures. Thus, such an antimicrobial is more easily controlled, as discussed above, for surface release as desired. Such agents include, without limitation, silver salts, silver oxides, elemental silver, and, most preferably ion exchange, glass, and/or zeolite compounds. Of even greater preference are silver-based ion exchange compounds for this purpose due to the low levels of discoloration and enhanced durability in the final product provided by such compounds, the efficacy provided to the final formulation with such a compound, and the ease of manufacture permitted with such specific compounds. Thus, the antimicrobial agent of this invention may be any type which imparts the desired log kill rates as previously discussed to *Staphylococcus aureus*, *Klebsiella pneumoniae*, *Escherichia coli*, and *Pseudomonas aeruginosa*, as merely representative organisms. Furthermore, such antimicrobial compounds must be able to withstand elevated processing temperatures for successful incorporation within the target non-sulfur (peroxide, for example) cured rubber formulations. Again, such antimicrobial agents comprise, preferably, silver-containing ion exchange, glass, and/or zeolite compounds. Most preferably, such a compound is a silver-based ion-exchange compound and particularly does not include any added organic bactericide compounds (thereby not permitting a release of volatile organic compounds into the atmosphere during processing at high temperatures, etc.). The preferred silver-based ion exchange material is an antimicrobial silver zirconium phosphate available from Milliken & Company, under the trade name ALPHASAN®. Such compounds are available in different silver ion concentrations as well as mixtures with zinc oxide. Thus, different compounds of from about 0.01 to 10% of silver ion concentration, preferably from about 3 to about 8%, and most preferably amounts of about 3, 3.8, and 10% by total amount of components (e.g. of the total amount of silver ions and zirconium phosphate) are possible. Other potentially preferred silver-containing solid inorganic antimicrobials in this invention are silver-substituted zeolite available from Sinanen under the tradename ZEOMIC®, or a silver-substituted glass available from Ishizuka Glass under the tradename IONPURE®, which may be utilized either in addition to or as a substitute for the preferred species. Other possible compounds, again without limitation, are silver-based materials such as MICROFREE®, available from DuPont, as well as JMAC®, available from Johnson Mathey.

Generally, such an antimicrobial compound is added to a rubber formulation in an amount of from about 0.1 to 10% by total weight of the particular total rubber formulation; preferably from about 0.1 to about 5%; more preferably from about 0.1 to about 2%; and most preferably from about 0.2 to about 2%.

Furthermore, with regard to silver-based inorganic antimicrobial materials, these particular antimicrobial rubber articles are shown to be particularly suitable for the desired high levels of efficacy and durability required of such articles. It has been found that certain silver-based ion exchange compounds, such as ALPHASAN® brand antimicrobials available from Milliken & Company, (U.S. Pat. No. 5,926,238, U.S. Pat. No. 5,441,717, U.S. Pat. No. 5,698,229 to Toagosei Chemical Industry Inc.), exhibit impressive bio-efficacy. After a period of time, alternative antimicrobial compounds (e.g. triclosan, Microchek, OBPA, Zn-omadine) initially suffer from decomposition under the high processing temperatures, followed by depletion of the biocide through leaching into the surrounding environment and finally through depleted bactericidal activity. However, silver-containing ion exchange, glass, and/or zeolite compounds do not suffer from these shortcomings. Such antimicrobial agents exhibit high temperature stability (>1000° C.), do not leach into the environment and provide substantial amounts of the oligodynamic silver ion to provide for the desired extensive durability.

The antimicrobial articles ultimately made from the inventive raw rubber formulations should exhibit an acceptable log kill rate after 24 hours in accordance with at least one method of either the AATCC Draft Method entitled "Assessment of Antimicrobial Properties on Hydrophobic Textiles and Solid Substrates" or Japanese Method JIS2 2801. Such an acceptable level log kill rate is tested for *Staphylococcus aureus* or *Klebsiella pneumoniae* of at least 0.1 increase over baseline. Alternatively, an acceptable level will exist if the log kill rate is greater than the log kill rate for non-treated (i.e., no solid inorganic antimicrobial added) rubber articles (such as about 0.5 log kill rate mcrease over control, antimicrobial-free rubbers). Preferably these log kill rate baseline increases are at least 0.3 and 0.3, respectively for *S. aureus* and *K. pneumoniae*; more preferably these log kill rates are 0.5 and 0.5, respectively; and most preferably these are 1.0 and 1.0, respectively. Of course, the high end of such log kill rates are much higher than the baseline, on the magnitude of 5.0 (99.999% kill rate). Any rate in between is thus, of course, acceptable as well. However, log kill rates which are negative in number are also acceptable for this invention as long as such measurements are better than that recorded for correlated non-treated rubber articles. In such an instance, the antimicrobial material present within the rubber article at least exhibits a hindrance to microbial growth. Furthermore, such rubber articles should exhibit log kill rates of the same degree for other types of bacteria, such as, *Psedumonas aeruginosa* and *Eschericia coli*.

Of great surprise within this invention is the ability for the finished articles made from the inventive raw rubber formulations to provide antifungal benefits as well as antibacterial characteristics. Such versatility is rare among antibacterial compounds; however, without intending to be limited to any particular scientific theory, it appears that the silver ions, and particularly the silver ions present at the article surface in great abundance, provide excellent antifungal properties, at least for certain fungi. Thus, another embodiment of this inventive rubber formulation should provide fungal kill durability of at least 15 sequential days for such organisms as *Aspergillus niger* and mixtures of fungi including *Aspergillus niger* ATCC 6275, *Paecilomyces variotii* ATCC 18502, *Trichoderna virens* ATCC 9645. In order to provide a greater array of potential antifungal benefits, other compounds may be incorporated within the target prevulcanized rubber formulation (and subsequent article), such as zinc oxide, as one example.

Of great importance to the effectiveness of the inventive formulation in terms of antimicrobial and antifungal activity is the omission of deleterious amounts of sulfur-based curing agents and accelerators from the inventive raw rubber formulation (and thus the vulcanized article). As noted above, sulfur reacts with the preferred silver-based antimicrobials and irreversibly binds the silver ions (as silver sulfides, for example) within the rubber composition and/or article itself. As such, the resultant silver sulfides, etc., are ineffective as antimicrobial agents and their presence thus renders the final product antimicrobially inactive. Thus, it has been necessary to produce a vulcanized rubber article lacking any appreciable amount of sulfur curing agents and accelerators therein. It should be appreciated that the term "appreciable amount" permits a small amount to be present. It has been found that, as a molar ratio, a 1:1 ratio (and above) between sulfur molar presence and silver molar presence results in a clear loss of antimicrobial activity within the desired ultimate vulcanized article. However, greater molar amounts of silver in relation to sulfur provide at least some antimicrobial properties to the desired article. A molar ratio range of from 0.25:1 to about 0.000000001:1 of sulfur to silver ions is thus at least acceptable. The primary curing agent, however, must be of non-sulfur nature (and is preferably, though not necessarily) a peroxide-based compound in order to provide the desired antimicrobial activity for the subject rubber. Although peroxide curing agents have been utilized for vulcanization of rubber previously, such a different type of curing agent is not widely utilized as a suitable vulcanization catalyst for rubber for a number of reasons. Foremost, such curing agents are much more costly than standard sulfur-based agents and thus the utilization of such peroxides, and the like, as a replacement for the sulfur-based compounds have been rather limited to mostly silicone-based rubbers or, at the very least, non-antibacterial rubber articles. However, due to the problems associated with antimicrobial activity when such compounds are reacted with sulfur-based curing agents, alternatives to such sulfur-based cured articles was to permit utilization of such effective antimicrobial compounds within raw and vulcanized rubber for long-tern high log kill rate effects. Thus, although non-sulfur-based compounds are not readily utilized within the non-silicone industry as vulcanization curing agents, utilization of such curing agents was necessary to provide an effective, ultimate antimicrobial vulcanized rubber article.

Surprisingly, it has now been found that the inventive rubber formulations listed above are available without such sulfur-based curing agents in any appreciable amounts; most importantly, with the introduction of certain additives, the structural integrity of the rubber formulation is improved to an acceptable level and the efficacy of the antimicrobial components can be controlled simultaneously.

Thus, the curing agent present within the inventive raw unvulcanized rubber formulation must be at least a majority, and preferably at least about 75% by weight of a non-sulfur-based curing agent. As discussed above, traditional sulfur and sulfur-based catalysts will not work with the inventive antimicrobial formulations due to chemical reactions between the sulfur atoms and and the biocidal Ag+ion. However, non-sulfur-based catalysts, such as, for example, and without intending to being limited to peroxides, certain compounds provide effective curing for the inventive raw rubber formulations, such as organic peroxides, including dicumyl peroxide, 2,5-bis(t-butylperoxy)-2.5-dimethylhexane, di-(t-butyl-peroxy-isopropyl)benzene, di-(t-butyl-peroxy-trimethyl)-cyclohexane, and the like, and inorganic oxides and/or peroxides, including zinc oxide, zinc peroxide, and the like. Such a curing agent should be present in amount of from about 0.5 to about 100 parts per hundred parts of rubber (pphr); more preferably from about 1 to about 50 pphr; and most preferably from about 2 to about 10 pphr, all either as one curing agent alone, or as the combination of any number of different types.

Other additives to the rubber formulation include any of the aforementioned silver ion release control additives, as well as accelerators, accelerator activators, antidegradants, softeners, abrasives, colorants, flame retardants, homogenizing agents, internal lubricants, and deodorants. Such components should be present, if at all, in rather low amounts, of from about 0.1 to about 100 pphr.

It has further been unexpectedly determined that a substantial increase in the antibacterial and antifungal efficacy is provided upon washing the finished article. Abrading the surface of such an article also permits increases in such characteristics; however, industrial laundering of certain rubber products (mats, and the like) can be improved in antimicrobial, etc., efficacy through a simple washing. In fact, such an increase steadily improves with greater numbers of consistent washes such that it has been found that a rubber article as first vulcanized exhibits lower overall antibacterial and antifungal activity than one that has been washed one, two, three, and up to at least 20 times (in a standard industrial rotary washing machine). Such a surprising benefit thus permits utilization of such rubber articles as floor coverings (mats, as one example, such as those with carpeted portions or those which are rubber alone; particularly foamed rubber mats for antifatigue properties and reduced specific gravity so as to reduce the chances of machinery damage during such industrial rotary launderings and dryings), and other articles which can be easily washed within standard laundry machines.

Furthermore, as alluded to above, friction with the subject rubber article surface can remove very slight layers of rubber from the article surface thereby permitting "fresh" silver-comprising crystallites to the surface to act as desired in their antibacterial and/or antifungal capacities. Basically, then, the inventive article produced from the inventive raw rubber formulation exhibits an even dispersion of antimicrobial particles throughout the entire rubber article. Such an even dispersion of the biocide throughout the rubber article thus provides a reservoir of fresh crystallites containing the biocidal metallic ion. As layers of the rubber are worn and abraded away, antimicrobial particles containing untapped silver ions become available.

The preferred peroxide cured rubber articles made from the inventive raw rubber formulations containing the antimicrobial agent can be processed into rubber articles which exhibit excellent antimicrobial qualities as well as antimicrobial efficiency throughout the rubber article's lifetime. Examples of other such rubber articles encompassed within this invention include, but are not limited to hard rubber mats, static dissipative rubber mats, anti-fatigue rubber mats, rubber mats which include a face fiber, rubber link mats, rubber gaskets, rubber medical goods, rubber containing bandages, medical devices, conveyor belts, rubber gloves, rubber belts and rubber wheels used in food processing, rubber clothing, rubber shoes, rubber boots, rubber tubing, and rubber automotive fuel hoses. Such inventive formulations may also be incorporated into a multilayered rubber article in which the antimicrobial agent can be incorporated into any surface layer and still provide the desired antimicrobial efficiency.

Of particular interest is the formation of multilayered rubber articles wherein at least one of such rubber layer exhibits the desired antimicrobial activity and thus is made from an inventive raw rubber formulation. Such layered articles may be adhered together through co-vulcanization, gluing, and the like. Furthermore, layers of other types of materials may be placed being rubber layers as well to provide, as one non-limiting property, better structural stability to the desired multilayered article.

The non-limiting preferred embodiments of these rubber formulations are discussed in greater detail below.

DESCRIPTION OF THE PREFERRED EMBODIMENTS

Inventive Raw Rubber Formulations: (pphr=parts per hundred rubber)

(INVENTIVE) EPDM BASE FORMULATION 1

| Component | Amount |
| --- | --- |
| Ethylene-propylene diene modified Rubber (Nordel IP from DuPont-Dow) | 100 parts |
| Pentaerythritol tetrastearate (processing aid) | 2 pphr |
| FEF N550 (CABOT carbon black filler) | 100 pphr |
| Silica | 50 pphr |
| Stearic acid | 0.5 pphr |
| Zinc oxide | 5 pphr |
| Calcium carbonate | 50 pphr |
| Paraffinic oil | 50 pphr |
| Ethyleneglycol dimethacrylate | 2.5 pphr |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) EPDM BASE FORMULATION 2

| Component | Amount |
| --- | --- |
| Ethylene-propylene diene modified Rubber | 100 parts |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) EPDM BASE FORMULATION 3

| Component | Amount |
| --- | --- |
| Ethylene-propylene diene modified Rubber | 100 parts |
| FEF N550 (CABOT carbon black filler) | 100 pphr |
| Paraffinic oil | 50 pphr |
| di-(tert-butyl-peroxy-isopropyl)benzene | 4 pphr |
| di-(tert-butyl-peroxy-trimenthyl)-cyclohexane | 4 pphr |
| Antimicrobial | as noted |

(INVENTIVE) EPDM BASE FORMULATION 4

| Component | Amount |
| --- | --- |
| Ethylene-propylene diene modified Rubber (from DuPont-Dow) | 100 parts |
| Silica | 50 pphr |
| Paraffinic oil | 50 pphr |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) EPDM BASE FORMULATION 5

| Component | Amount |
| --- | --- |
| Ethylene-propylene diene modified Rubber | 100 parts |
| Pentaerythritol tetrastearate (processing aid) | 2 pphr |
| Silica | 50 pphr |
| Stearic acid | 0.5 pphr |
| Zinc oxide | 10 pphr |
| Calcium carbonate | 50 pphr |
| Paraffinic oil | 30 pphr |
| Ethyleneglycol dimethacrylate | 45 pphr |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) EPDM BASE FORMULATION 6

| Component | Amount |
| --- | --- |
| Ethylene-propylene diene modified Rubber | 100 parts |
| Pentaerythritol tetrastearate (processing aid) | 2 pphr |
| Blue organic pigment | 2 pphr |
| Silica | 50 pphr |
| Stearic acid | 0.5 pphr |
| Zinc oxide | 5 pphr |
| Calcium carbonate | 50 pphr |
| Paraffinic oil | 50 pphr |
| Ethyleneglycol dimethacrylate | 4 pphr |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) NBR BASE FORMULATION 1

| Component | Amount |
|---|---|
| Acrylonitrile butadiene Rubber (from Zeon Chemicals) | 100 parts |
| FEF N550 | 50 pphr |
| Stearic acid | 1 pphr |
| Microcrystalline wax | 2 pphr |
| Polyethylene glycol | 5 pphr |
| Silica | 40 pphr |
| Zinc oxide | 5 pphr |
| Calcium carbonate | 20 pphr |
| di-octyl-phthalate | 3 pphr |
| di-(tert-butyl-peroxy-isopropyl)benzene | 4 pphr |
| di-(tert-butyl-peroxy-trimethyl)-cyclohexane | 4 pphr |
| Antimicrobial | as noted |

(INVENTIVE) NBR BASE FORMULATION 2

| Component | Amount |
|---|---|
| Acrylonitrile butadiene Rubber | 100 parts |
| Pentaerythritol tetrastearate (processing aid) | 1 pphr |
| Microcrystalline wax | 1 pphr |
| FEF N550 | 50 pphr |
| Silica | 20 pphr |
| Stearic acid | 1 pphr |
| Zinc oxide | 5 pphr |
| Calcium carbonate | 20 pphr |
| di-octyl-phthalate | 20 pphr |
| Celogen ® ADCK (Blowing agent) | 3 pphr |
| Celogen ® OB (Blowing agent) | 3 pphr |
| di-(tert-butyl-peroxy-isopropyl)benzene | 3 pphr |
| di-(tert-butyl-peroxy-trimethyl)-cyclohexane | 3 pphr |
| Antimicrobial | as noted |

(INVENTIVE) NATURAL RUBBER BASE FORMULATION

| Component | Amount |
|---|---|
| Natural Rubber | 100 parts |
| Pentaerythritol tetrastearate (processing aid) | 2 pphr |
| Polyethylene glycol | 5 pphr |
| Silica | 40 pphr |
| Calcium oxide (dessicant) | 10 pphr |
| Titanium dioxide | 5 pphr |
| Zinc oxide | 3 pphr |
| Calcium carbonate | 20 pphr |
| Paraffinic oil | 20 pphr |
| Ethyleneglycol dimethacrylate | 2.5 pphr |
| di-(tert-butyl-peroxy-isopropyl)benzene | 1 pphr |
| di-(tert-butyl-peroxy-trimethyl)-cyclohexane | 1 pphr |
| Antimicrobial | as noted |

Specific samples with different silver ion-exchange zirconium phosphate salts (available from Milliken & Company under the tradename ALPHASAN®) were made from these base formulations and are listed below. The different biocides presented throughout are labeled in accordance with the following table:

TABLE

| Biocide | Silver ion concentration | Other components (% by weight) |
|---|---|---|
| A | 3.8% | $Ag_xNa_yH_zZr_2(PO_4)_3$ where $x + y + z = 1$ |
| B | 10.0% | $Ag_xNa_yH_zZr_2(PO_4)_3$ where $x + y + z = 1$ |
| C | 3.0% | Zinc oxide (70%)(with 30% biocide B) |

The compounding of ingredients within each formulation can be carried out in an open mill, an internal mixer, or an extruder where intensive mixing within the polymer matrix of each component will take place. During the mixing operation, the control of temperature rise, due to high shear incorporation of the ingredients, is crucial to ensure that pre-vulcanization (scorch) does not take place during processing. Generally, a maximum temperature of 120° C. is reached on single stage (pass) mixing through an internal mixer. The compounds can be further processed after mixing into specific forms to allow adequate presentation for manufacturing into products. This could be calendering, extrusion, granulation/pelletization, strip form, fabrication and preforming into specific shaped blanks.

The vulcanization of the compounds can be in the form of molding (compression, transfer, injection), continuous extrusion (LCM, UHF[where permissible], autoclave and hot air), and coatings. The vulcanization (cure) temperatures can range from 150° C. to 250° C. In this specific situation, the rubber articles were calendared into rough mat structures and then subjected to vulcanization under high temperature and pressure.

Testing of Vulcanized Rubber Articles

The following Tables list the antibacterial and antifungal activity of these inventive and comparative samples. The antimicrobial tests followed were AATCC Draft Test Method "Assessment of Antimicrobial Properties on Hydrophobic Textiles and Solid Substrates" and Japanese Method JIS2 2801 for *Staphylococcus aureus* and the antifungal tests followed were ISO 486 for *Aspergillus niger* and a mixture of fungi including *Aspergillus niger, Paecilomyces variotii,* and *Trichoderma virens*. Further tests, such as silver-ion extraction within an aqueous salt solution and testing the liquor for any extracted silver ions therein under inductively coupled plasma methods, were followed to analyze the effectiveness of certain additives (silica, carbon black, phthalate oils) in relation to antimicrobial efficacy as well. Lastly, industrial washing of such mats was undertaken in an effort to determine the improvements (if any) of the antimicrobial activity of certain samples.

EXPERIMENTAL TABLE 1

Antimicrobial Performance of Rubber Formulations for *Staphylococcus aureus* and *Klebsiella pneumoniae*

EXPERIMENTAL TABLE 1

Antimicrobial Performance of rubber formulations for *Staphylococcus aureus* and *Klebsiella pneumoniae*

| | | log kill reduction vs. internal control | |
|---|---|---|---|
| Sample ID | biocide ID | S. aureus | K. pneumoniae |
| EPDM Formulation 2 | no biocide | 0.66 | 1.35 |
| EPDM Formulation 2 | 2% biocide B | 3.27 | 5.21 |

EXPERIMENTAL TABLE 1-continued

Antimicrobial Performance of rubber formulations for *Staphylococcus aureus* and *Klebsiella pneumoniae*

| | | log kill reduction vs. internal control | |
|---|---|---|---|
| Sample ID | biocide ID | S. aureus | K. pneumoniae |
| EPDM Formulation 2 | 2% biocide C | 3.27 | 5.21 |
| EPDM Formulation 3 | no biocide | 0 | −0.28 |
| EPDM Formulation 3 | 2% biocide B | 2.85 | 4.25 |
| EPDM Formulation 4 | no biocide | 0 | −0.21 |
| EPDM Formulation 4 | 2% biocide B | 2.85 | 4.25 |
| NBR Formulation 1 | no biocide | NA | 0 |
| NBR Formulation 2 | 1% biocide A | NA | 3.87 |
| NBR Formulation 1 | 1% biocide C | NA | 4.01 |
| Natural Rubber Formulation | no biocide | NA | −1.98 |
| Natural Rubber Formulation | 1% biocide A | NA | −1.62 |
| Natural Rubber Formulation | 1% biocide C | NA | −1.19 |

Thus, the inventive formulations provided inventive vulcanized rubber articles that exhibited improved antimicrobial activity over the same formulations without any antimicrobial compounds present.

EXPERIMENTAL TABLE 2

Antifungal Performance of Inventive Rubber Articles

EXPERIMENTAL TABLE 2

Antifungal Performance of Inventive Rubber Articles

| | | Fungal Growth After | | | | |
|---|---|---|---|---|---|---|
| | | 0 | 5 | 10 | 15 | 20 |
| EPDM no biocide | *Aspergillus niger* | 0 | 4 | 4 | 4 | 4 |
| EPDM Formulation 5 | *Aspergillus niger* | 0 | 0 | 0 | 0 | 0 |
| EPDM Formulation 6 | *Aspergillus niger* | 0 | 0 | 0 | 0 | 0 |
| NBR Formulation 1 | *Aspergillus niger* | 0 | 0 | 0 | 0 | 0 |
| EPDM no biocide | mixture* | 0 | 4 | 4 | 4 | 4 |
| EPDM Formulation 5 | mixture* | 0 | 0 | 0 | 0 | 0 |
| EPDM Formulation 6 | mixture* | 0 | 0 | 2 | 2 | 3 |
| NBR Formulation 1 | mixture* | 0 | 0 | 1 | 2 | 3 |

Efficacy against fungi was assessed using ISO Method 846 against *Aspergillus niger* ATCC 6275. The mixture of fingi includes *Aspergillus niger* ATCC 6275, *Paecilomyces variotii* ATCC 18502, *Trichoderma virens* ATCC 9645. Samples were placed on Potato Dextrose Agar (PDA) and inoculated with 10 droplets (10 ul each, 100 ul total) of 10E5 fungal spores/ml in a synthetic nutrient medium followed by incubation for 7–20 days at 30° C. and >90% relative humidity. Efficacy was measured by visual observation of the samples.

| Observation | Rating |
|---|---|
| None | 0 |
| Traces of Growth (less than 10%) | 1 |
| Light Growth (10–30%) | 2 |
| Medium Growth (30–60%) | 3 |
| Heavy Growth (60% to complete coverage) | 4 |

EXPERIMENTAL TABLE 3

Antimicrobial Activity of Inventive NBR Formulation Articles After Industrial Washing.

| Sample ID | biocide | wash cycles | K. pneumoniae | S. aureus |
|---|---|---|---|---|
| NBR Formulation 1 | no biocide | 0 wash | −0.33 | −0.10 |
| NBR Formulation 1 | no biocide | 1 wash | −0.72 | −0.14 |
| NBR Formulation 1 | no biocide | 20 wash | −0.37 | −0.09 |
| NBR Formulafion 1 | 1% biocide A | 0 wash | −0.01 | 0.16 |
| NBR Formulation 1 | 1% biocide A | 1 wash | 3.67 | 2.17 |
| NBR Formulation 1 | 1% biocide A | 20 wash | 4.15 | 2.08 |
| NBR Formulation 2 | 1.5% biocide A | 0 wash | −0.48 | NA |
| NBR Formulation 2 | 1.5% biocide A | 1 wash | −0.56 | NA |
| NBR Formulation 2 | 1.5% biocide A | 20 wash | 3.54 | 3.77 |

Thus, the inventive articles not only retained the antimicrobial and thus exhibited antimicrobial activity after washing, such activity actually and unexpectedly improved as the number of washes increased. This indicates that the amount of effective antimicrobial silver ions available at the target article surface increased as the number of washings increased. In fact, this was measured through silver ion extraction methods and found to be true for the above samples. The results are as follows:

EXPERIMENTAL TABLE 3

Antimicrobial Activity of Inventive NBR Formulation Articles After Industrial Washing.

| Sample ID | biocide | wash cycles | ppb of bio-available $Ag^+/cm^2$ |
|---|---|---|---|
| NBR Formulation 1 | no biocide | 0 wash | 0 |
| NBR Formulation 1 | no biocide | 1 wash | 0 |
| NBR Formulation 1 | no biocide | 20 wash | 0 |
| NBR Fonnulation 1 | 1% biocide A | 0 wash | 0.02 |
| NBR Formulation 1 | 1% biocide A | 1 wash | 0.7 |
| NBR Formulation 1 | 1% biocide A | 20 wash | 1.68 |
| NBR Formulation 2 | 1.5% biocide A | 0 wash | 0.07 |
| NBR Formulation 2 | 1.5% biocide A | 1 wash | 0.23 |
| NBR Formulation 2 | 1.5% biocide A | 20 wash | 1.87 |

Antimicrobial Control Through Filler and Plasticizer Use as Well as Surface Abrasion Of great interest and of highly unexpected nature, it was found that the amount of available antimicrobial present at the rubber article surface after initial production was greatly increased with the presence of certain fillers and oils within the rubber formulation. The affect of abrading the surface of one article through the contacting random portions of the target article surface with a sanding block for approximately 5 seconds is also shown. The target article was immersed in an aqueous salt extraction solution (sodium chloride) for 24 hours; the extract was then analyzed by inductively coupled plasma measurements for a measurement of available silver removed from the article surface. The following table illustrates these measurements:

EXPERIMENTAL TABLE 4

| Example | Surface Abraded? (Y/N) | Available Ag + ions (ppb/cm$^2$) |
|---|---|---|
| EPDM Base Formulation 2 | N | 2.4 |
| EPDM Base Formulation 3 | N | 0.41 |
| EPDM Base Formulation 4 | N | 271.4 |
| EPDM Base Formulation 4 | Y | 306.4 |

Thus, the inventive articles exhibited controlled release of silver ions dependent upon the presence of different fillers and oils, with the greatest increase occurring with the addition of silica and paraffinic oil with an even greater increase in potential antimicrobial efficacy through the utilization of an abrasion procedure to the article surface.

Having described the invention in detail it is obvious that one skilled in the art will be able to make variations and modifications thereto without departing from the scope of the present invention. Accordingly, the scope of the present invention should be determined only by the claims appended hereto.

What is claimed is:

1. A pre-vulcanized rubber formulation comprising at least one rubber constituent, the majority of which must be a non-silicone rubber, at least one silver-based antimicrobial compound, and at least one curing compound, wherein all of said curing compounds present within said formulation does not include an appreciable amount of sulfur-based compounds; wherein said rubber formulation optionally comprises at least one blowing agent, at least one silver ion release control additive, and at least one antifungal additive other than said silver-based antimicrobial compound.

2. The rubber formulation of claim 1 wherein said rubber constituent is selected from the group consisting of ethylene-propylene diene monomer (EPDM) rubber, nitrile butadiene rubber (NBR), natural rubber, and any mixture thereof.

3. The rubber formulation of claim 1 wherein said silver-based antimicrobial compound is selected from the group consisting of elemental silver, silver oxides, silver salts, silver ion exchange compounds, silver zeolites, silver glasses, and any mixtures thereof.

4. The rubber formulation of claim 2 wherein said silver-based antimicrobial compound is selected from the group consisting of elemental silver, silver oxides, silver salts, silver ion exchange compounds, silver zeolites, silver glasses, and any mixtures thereof.

5. The rubber formulation of claim 1 wherein said curing compound comprises a majority amount by weight of at least one peroxide.

6. The rubber formulation of claim 5 wherein said peroxide is an organic peroxide.

7. The rubber formulation of claim 2 wherein said curing compound comprises a majority amount by weight of at least one peroxide.

8. The rubber formulation of claim 7 wherein said peroxide is an organic peroxide.

9. The rubber formulation of claim 3 wherein said curing compound comprises a majority amount by weight of at least one peroxide.

10. The rubber formulation of claim 9 wherein said peroxide is an organic peroxide.

11. The rubber formulation of claim 4 wherein said curing compound comprises a majority amount by weight of at least one peroxide.

12. The rubber formulation of claim 11 wherein said peroxide is an organic peroxide.

13. The rubber formulation of claim 1 wherein said at least one blowing agent is present.

14. The rubber formulation of claim 1 wherein said at least one silver ion control release additive is present.

15. The rubber formulation of claim 1 wherein said antifungal additive other than said silver-based antimicrobial compound is present.

16. The rubber formulation of claim 14 where said at least one silver ion control release additive is selected from the group consisting of fillers, oils, pigments, salts, antistatic agents, and any mixtures thereof.

17. The rubber formulation of claim 16 wherein said at least one silver ion control release additive is a hydrophilic filler selected from the group consisting of silica, stearates, and any mixtures thereof.

18. The rubber formulation of claim 16 further comprising at least one oil selected from the group consisting of paraffinic oil, phthalate oil, and any mixtures thereof.

19. The rubber formulation of claim 2 wherein said rubber constituent is EPDM.

20. The rubber formulation of claim 2 wherein said rubber constituent is NBR.

21. The rubber formulation of claim 2 wherein said rubber constituent is natural rubber.

22. A method of producing a rubber article exhibiting long-lasting, regenerable antimicrobial characteristics, comprising the steps of compounding together the unvulcanized rubber formulation of claim 1, molding said rubber formulation into a preselected shape, and vulcanizing said rubber formulation.

23. A method of producing a rubber article exhibiting long-lasting, regenerable antimicrobial characteristics, comprising the steps of compounding together the unvulcanized rubber formulation of claim 2, molding said rubber formulation into a preselected shape, and vulcanizing said rubber formulation.

24. A method of producing a rubber article exhibiting long-lasting, regenerable antimicrobial characteristics, comprising the steps of compounding together the unvulcanized rubber formulation of claim 13, molding said rubber formulation into a preselected shape, and vulcanizing said rubber formulation.

25. A method of producing a rubber article exhibiting long-lasting, regenerable antimicrobial characteristics, comprising the steps of compounding together the unvulcanized rubber formulation of claim 14, molding said rubber formulation into a preselected shape, and vulcanizing said rubber formulation.

26. A method of producing a rubber article exhibiting long-lasting, regenerable antimicrobial characteristics, comprising the steps of compounding together the unvulcanized rubber formulation of claim 15, molding said rubber formulation into a preselected shape, and vulcanizing said rubber formulation.

27. A rubber composition comprising at least one rubber component, at least one peroxide curing agent, and at least one silver-based antimicrobial agent, and optionally comprising at least one blowing agent, at least one silver ion release control additive, and at least one antifungal additive other than said silver-based antimicrobial compound.

* * * * *